(12) United States Patent
Rabinowitz et al.

(10) Patent No.: US 6,783,753 B2
(45) Date of Patent: Aug. 31, 2004

(54) DELIVERY OF ANTIDEPRESSANTS THROUGH AN INHALATION ROUTE

(75) Inventors: Joshua D. Rabinowitz, Mountain View, CA (US); Alejandro C. Zaffaroni, Atherton, CA (US)

(73) Assignee: ALEXZA Molecular Delivery Corporation, Palo Alto, CA (US)

( * ) Notice: Subject to any disclaimer, the term of this patent is extended or adjusted under 35 U.S.C. 154(b) by 31 days.

(21) Appl. No.: 10/151,626

(22) Filed: May 16, 2002

(65) Prior Publication Data

US 2003/0206869 A1 Nov. 6, 2003

Related U.S. Application Data

(60) Provisional application No. 60/317,479, filed on Sep. 5, 2001, and provisional application No. 60/294,203, filed on May 24, 2001.

(51) Int. Cl.[7] .............................. A61K 9/12; A61K 9/14
(52) U.S. Cl. ............................ 424/45; 424/46; 424/43; 128/200.14; 128/200.24
(58) Field of Search .............................. 424/45, 46, 43, 424/489; 128/200.14, 200.24, 203.12; 514/220

(56) References Cited

U.S. PATENT DOCUMENTS

| | | | |
|---|---|---|---|
| RE30,285 E | | 5/1980 | Babington |
| 5,292,499 A | | 3/1994 | Evans et al. |
| 5,388,574 A | * | 2/1995 | Ingebrethsen .......... 125/203.17 |
| 5,544,646 A | | 8/1996 | Lloyd et al. |
| 5,655,523 A | | 8/1997 | Hodson et al. |
| 5,694,919 A | | 12/1997 | Rubsamen et al. |
| 5,735,263 A | | 4/1998 | Rubsamen et al. |
| 5,758,637 A | | 6/1998 | Ivri et al. |
| 5,915,378 A | | 6/1999 | Lloyd et al. |
| 5,934,272 A | | 8/1999 | Lloyd et al. |
| 5,957,124 A | | 9/1999 | Lloyd et al. |
| 5,960,792 A | | 10/1999 | Lloyd et al. |
| 6,041,777 A | * | 3/2000 | Faithfull et al. ....... 128/200.24 |
| 6,095,153 A | | 8/2000 | Kessler et al. |
| 6,102,036 A | | 8/2000 | Slutsky et al. |
| 6,140,323 A | | 10/2000 | Ellinwood, Jr. et al. |
| 6,306,431 B1 | | 10/2001 | Zhang et al. |
| 6,420,351 B1 | | 7/2002 | Tsai et al. |
| 6,514,482 B1 | * | 2/2003 | Bartus et al. ................. 424/45 |
| 6,591,839 B2 | | 7/2003 | Meyer et al. |
| 2002/0058009 A1 | | 5/2002 | Bartus et al. |
| 2003/0032638 A1 | | 2/2003 | Kim et al. |

FOREIGN PATENT DOCUMENTS

| | | |
|---|---|---|
| EP | 0 358 114 | 3/1990 |
| WO | WO 91/07947 | 6/1991 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/37198 | 11/1996 |
| WO | WO 97/27804 | 8/1997 |
| WO | WO 98/22170 | 5/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/41732 | 6/2001 |
| WO | WO 01/95903 | 12/2001 |
| WO | WO 02/24158 | 3/2002 |

OTHER PUBLICATIONS

Office Action mailed Aug. 13, 2003 for US application 10/153,313 filed May 21, 2002 "Delivery of Benzodiazepines Through an Inhalation Route".

Bennett, R.L. et al. (1981). "Patient–Controlled Analgesia: A New Concept of Postoperative Pain Relief," *Annual Surg.* 195(6):700–705.

Carroll, M.E. et al. (1990), "Cocaine–base smoking in rhesus monkeys: reinforcing and physiological effects," *Psychopharmacology* (Berl). 102:443–450.

Clark, A. and Byron, P. (1986), "Dependence of Pulmonary Absorption Kinetics on Aerosol Particle Size," *Z. Erkrank.* 166:13–24.

(List continued on next page.)

Primary Examiner—Michael G. Hartley
Assistant Examiner—Mina Haghighatian
(74) Attorney, Agent, or Firm—Elaine C. Stracker

(57) ABSTRACT

The present invention relates to the delivery of antidepressants through an inhalation route. Specifically, it relates to aerosols containing an antidepressant that are used in inhalation therapy. In a composition aspect of the present invention, the aerosol comprises particles comprising at least 5 percent by weight of an antidepressant. In a method aspect of the present invention, an antidepressant is delivered to a mammal through an inhalation route. The method comprises: a) heating a composition, wherein the composition comprises at least 5 percent by weight of an antidepressant to form a vapor; and, b) allowing the vapor to cool, thereby forming a condensation aerosol comprising particles, which is inhaled by the mammal. In a kit aspect of the present invention, a kit for delivering an antidepressant through an inhalation route to a mammal is provided which comprises: a) a composition comprising at least 5 percent by weight of an antidepressant; and, b) a device that forms an antidepressant containing aerosol from the composition, for inhalation by the mammal.

13 Claims, 1 Drawing Sheet

OTHER PUBLICATIONS

Darquenne, C. et al. (1997). "Aerosol Dispersion in Human Lung: Comparison Between Numerical Simulations and Experiments for Bolus Tests," *American Physiological Society*, 966–974.

Davies, C.N. et al. (May 1972). "Breathing of Half–Micron Aerosols," *Journal of Applied Physiology*. 32(5):591–600.

Dershwitz, M., M.D., et al. (Sep. 2000). "Pharmacokinetics and Pharmacodynamics of Inhaled versus Intravenous Morphine in Healthy Volunteers," *Anesthesiology*. 93(3): 619–628.

Finlay, W.H. (2001). "The Mechanics of Inhaled Pharmaceutical Aerosols", Academic Press: San Diego Formula 2.39. pp. 3–14 (Table of Contents). pp. v –viii.

Gonda,I. (1991). "Particle Deposition in the Human Respiratory Tract," Chapter 176, *The Lung: Scientific Foundations*. Crystal R.G. and West, J.B. (eds.), Raven Publishers, New York. pp. 2289–2294.

Hatsukami D, et al. (May 1990) "A method for delivery of precise doses of smoked cocaine–base to humans." *Pharmacology Biochemistry & Behavior*. 36(1):1–7.

Heyder, J. et al. (1986). "Deposition of Particles in the Human Respiratory Tract in the Size Range 0.005–15 $\mu$m," *J. Aerosol Sci.* 17(5):811–822.

Huizer, H., "Analytical studies on illicit heron. V. Efficacy of volatilization during heroin smoking." *Pharmaceutisch Weekblad Scientific Edition* (1987). 9(4):203–211.

Hurt, R.D., MD and Robertson, C.R., PhD, (Oct. 1998). "Prying Open the Door to the Tobacco Industry's Secrets About Nicotine: The Minnesota Tobacco Trial," *JAMA* 280(13):1173–1181.

Lichtman, A.H. et al. (1996). "Inhalation Exposure to Volatilized Opioids Produces Antinociception in Mice," Journal of Pharmacology and Experimental Therapeutics. 279(1):69–76.

Martin, B.R. and Lue, L.P. (May/Jun. 1989). "Pyrolysis and Volatilization of Cocaine," *Journal of Analytical Toxicology* 13:158–162.

Mattox, A.J. and Carroll, M.E., (1996). "Smoked heroin self–administration in rhesus monkeys," *Psychopharmacology*, 125:195–201.

Meng, Y, et al. "Inhalation Studies With Drugs of Abuse," *NIDA Research Monograph*, (1997) 173:201–224.

Meng, Y., et al. (1999). "Pharmacological effects of methamphetamine and other stimulants via inhalation exposure," *Drug and Alcohol Dependence*. 53:111–120.

Pankow, J.F. et al. (1997). "Conversion of Nicotine in Tobacco Smoke to Its Volatile and Available Free–Base Form Through the Action of Gaseous Ammonia," *Envron. Sci. Technol.* 31:2428–2433.

Pankow, J. (Mar. 2000). ACS Conference–San Francisco– Mar. 26, 2000. Chemistry of Tobacco Smoke. pp. 1–8.

Seeman, J. et al. (1999). "The Form of Nicotine in Tobacco. Thermal Transfer of Nicotine and Nicotine Acid Salts to Nicotine in the Gas Phase," *J. Agric. Food Chem.* 47(12):5133–5145.

Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271–1280.

Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," *Clinical Pharmacology & Therapeutics* 62(6):596–609.

Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior*. 55(2):237–248.

* cited by examiner

DELIVERY OF ANTIDEPRESSANTS THROUGH AN INHALATION ROUTE

This application claims priority to U.S. provisional application Serial No. 60/294,203 entitled "Thermal Vapor Delivery of Drugs," filed May 24, 2001, Rabinowitz and Zaffaroni, the entire disclosure of which is hereby incorporated by reference. This application further claims priority to U.S. provisional application Serial No. 60/317,479 entitled "Aerosol Drug Delivery," filed Sep. 5, 2001, Rabinowitz and Zaffaroni, the entire disclosure of which is hereby incorporated by reference.

FIELD OF THE INVENTION

The present invention relates to the delivery of antidepressants through an inhalation route. Specifically, it relates to aerosols containing antidepressants that are used in inhalation therapy.

BACKGROUND OF THE INVENTION

There are a number of compositions currently marketed as antidepressants. The compositions contain at least one active ingredient that provides for observed therapeutic effects. Among the active ingredients given in antidepressant compositions are bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, and protryptyline.

It is desirable to provide a new route of administration for antidepressants that rapidly produces peak plasma concentrations of the compound. The provision of such a route is an object of the present invention.

SUMMARY OF THE INVENTION

The present invention relates to the delivery of antidepressants through an inhalation route. Specifically, it relates to aerosols containing antidepressants that are used in inhalation therapy.

In a composition aspect of the present invention, the aerosol comprises particles comprising at least 5 percent by weight of an antidepressant. Preferably, the particles comprise at least 10 percent by weight of an antidepressant. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of an antidepressant.

Typically, the aerosol has a mass of at least 10 $\mu$g. Preferably, the aerosol has a mass of at least 100 $\mu$g. More preferably, the aerosol has a mass of at least 200 $\mu$g.

Typically, the particles comprise less than 10 percent by weight of antidepressant degradation products. Preferably, the particles comprise less than 5 percent by weight of antidepressant degradation products. More preferably, the particles comprise less than 2.5, 1, 0.5, 0.1 or 0.03 percent by weight of antidepressant degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the aerosol is formed by heating a composition containing an antidepressant to form a vapor and subsequently allowing the vapor to condense into an aerosol.

Typically, the antidepressant is selected from one of the following five classes of antidepressants: tricyclic antidepressants; tetracyclic antidepressants; selective serotonin reuptake inhibitors; monoamine oxidase inhibitors; and, atypical antidepressants.

In another composition aspect of the present invention, the aerosol comprises particles comprising at least 5 percent by weight of bupropion, nefazodone, perphenazine, trazodone, trimipramine, venlafaxine, tranylcypromine, citalopram, fluoxetine, fluvoxamine, mirtazepine, paroxetine, sertralinc, amoxapine, clomipramine, doxepin, imipramine, maprotiline, nortryptiline, valproic acid, or protryptyline. Preferably, the particles comprise at least 10 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

Typically, the aerosol has a mass of at least 10 $\mu$g. Preferably, the aerosol has a mass of at least 100 $\mu$g. More preferably, the aerosol has a mass of at least 200 $\mu$g.

Typically, the particles comprise less than 10 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products. Preferably, the particles comprise less than 5 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products. More preferably, the particles comprise less than 2.5, 1, 0.5, 0.1 or 0.03 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the aerosol comprises bupropion, the aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 20 mg/L and 150 mg/L.

Typically, where the aerosol comprises nefazodone, the aerosol has an inhalable aerosol drug mass density of between 5 mg/L and 250 mg/L. Preferably, the aerosol has an inhalable aerosol drug mass density of between 10 mg/L and 225 mg/L. More preferably, the aerosol has an inhalable aerosol drug mass density of between 20 mg/L and 200 mg/L.

Typically, where the aerosol comprises perphenazine, the aerosol has an inhalable aerosol drug mass density of between 0.2 mg/L and 5 mg/L. Preferably, the aerosol has an inhalable aerosol drug mass density of between 0.5 mg/L and 4 mg/L. More preferably, the aerosol has an inhalable aerosol drug mass density of between 0.5 mg/L and 3 mg/L.

Typically, where the aerosol comprises trazodone, the aerosol has an inhalable aerosol drug mass density of between 5 mg/L and 200 mg/L. Preferably, the aerosol has an inhalable aerosol drug mass density of between 10 mg/L and 150 mg/L. More preferably, the aerosol has an inhalable aerosol drug mass density of between 20 mg/L and 100 mg/L.

Typically, where the aerosol comprises trimipramine, the aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 20 mg/L and 150 mg/L.

Typically, where the aerosol comprises venlafaxine, the aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 20 mg/L and 100 mg/L.

Typically, where the aerosol comprises tranylcypromine, the aerosol has an inhalable aerosol drug mass density of between 3 mg/L and 30 mg/L. Preferably, the aerosol has an inhalable aerosol drug mass density of between 7.5 mg/L and 25 mg/L. More preferably, the aerosol has an inhalable aerosol drug mass density of between 7.5 mg/L and 20 mg/L.

Typically, where the aerosol comprises citalopram, the aerosol has an inhalable aerosol drug mass density of between 4 mg/L and 40 mg/L. Preferably, the aerosol has an inhalable aerosol drug mass density of between 10 mg/L and 35 mg/L. More preferably, the aerosol has an inhalable aerosol drug mass density of between 10 mg/L and 30 mg/L.

Typically, where the aerosol comprises fluoxetine, the aerosol has an inhalable aerosol drug mass density of between 4 mg/L and 40 mg/L. Preferably, the aerosol has an inhalable aerosol drug mass density of between 10 mg/L and 35 mg/L. More preferably, the aerosol has an inhalable aerosol drug mass density of between 10 mg/L and 30 mg/L.

Typically, where the aerosol comprises fluvoxamine, the aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises mirtazepine, the aerosol has an inhalable aerosol drug mass density of between 3 mg/L and 30 mg/L. Preferably, the aerosol has an inhalable aerosol drug mass density of between 7.5 mg/L and 25 mg/L. More preferably, the aerosol has an inhalable aerosol drug mass density of between 7.5 mg/L and 20 mg/L.

Typically, where the aerosol comprises paroxetine, the aerosol has an inhalable aerosol drug mass density of between 2 mg/L and 50 mg/L. Preferably, the aerosol has an inhalable aerosol drug mass density of between 5 mg/L and 40 mg/L. More preferably, the aerosol has an inhalable aerosol drug mass density of between 5 mg/L and 30 mg/L.

Typically, where the aerosol comprises sertraline, the aerosol has an inhalable aerosol drug mass density of between 5 mg/L and 100 mg/L. Preferably, the aerosol has an inhalable aerosol drug mass density of between 10 mg/L and 80 mg/L. More preferably, the aerosol has an inhalable aerosol drug mass density of between 15 mg/L and 50 mg/L.

Typically, where the aerosol comprises amoxapine, the aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 20 mg/L and 150 mg/L.

Typically, where the aerosol comprises clomipramine, the aerosol has an inhalable aerosol drug mass density of between 5 mg/L and 200 mg/L. Preferably, the aerosol has an inhalable aerosol drug mass density of between 10 mg/L and 150 mg/L. More preferably, the aerosol has an inhalable aerosol drug mass density of between 20 mg/L and 100 mg/L.

Typically, where the aerosol comprises doxepin, the aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 20 mg/L and 100 mg/L.

Typically, where the aerosol comprises imipramine, the aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 20 mg/L and 100 mg/L.

Typically, where the aerosol comprises maprotiline, the aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises nortriptyline, the aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises valproic acid, the aerosol has an inhalable aerosol drug mass density of between 20 mg/L and 1000 mg/L. Preferably, the aerosol has an inhalable aerosol drug mass density of between 50 mg/L and 500 mg/L. More preferably, the aerosol has an inhalable aerosol drug mass density of between 100 mg/L and 400 mg/L.

Typically, where the aerosol comprises protriptyline, the aerosol has an inhalable aerosol drug mass density of between 3 mg/L and 30 mg/L. Preferably, the aerosol has an inhalable aerosol drug mass density of between 5 mg/L and 25 mg/L. More preferably, the aerosol has an inhalable aerosol drug mass density of between 7.5 mg/L and 20 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the aerosol is formed by heating a composition containing bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline to form a vapor and subsequently allowing the vapor to condense into an aerosol.

In a method aspect of the present invention, an antidepressant is delivered to a mammal through an inhalation route. The method comprises: a) heating a composition, wherein the composition comprises at least 5 percent by weight of an antidepressant to form a vapor; and, b) allowing the vapor to cool, thereby forming a condensation aerosol comprising particles, which is inhaled by the mammal. Preferably, the composition that is heated comprises at least 10 percent by weight of an antidepressant. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antidepressant.

Typically, the particles comprise at least 5 percent by weight of an antidepressant. Preferably, the particles comprise at least 10 percent by weight of an antidepressant. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antidepressant.

Typically, the condensation aerosol has a mass of at least 10 $\mu$g. Preferably, the aerosol has a mass of at least 100 $\mu$g. More preferably, the aerosol has a mass of at least 200 $\mu$g.

Typically, the particles comprise less than 10 percent by weight of antidepressant degradation products. Preferably, the particles comprise less than 5 percent by weight of antidepressant degradation products. More preferably, the particles comprise 2.5, 1, 0.5, 0.1 or 0.03 percent by weight of antidepressant degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, the antidepressant is selected from one of the following five classes of antidepressants: tricyclic antidepressants; tetracyclic antidepressants; selective serotonin reuptake inhibitors; monoamine oxidase inhibitors; and, atypical antidepressants.

Typically, the delivered condensation aerosol results in a peak plasma concentration of antidepressant in the mammal in less than 1 h. Preferably, the peak plasma concentration is reached in less than 0.5 h. More preferably, the peak plasma concentration is reached in less than 0.2, 0.1, 0.05, 0.02, 0.01 h, or 0.005 h (arterial measurement).

In another method aspect of the present invention, one of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline is delivered to a mammal through an inhalation route. The method comprises: a) heating a composition, wherein the composition comprises at least 5 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline, to form a vapor; and, b) allowing the vapor to cool, thereby forming a condensation aerosol comprising particles, which is inhaled by the mammal. Preferably, the composition that is heated comprises at least 10 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

Typically, the particles comprise at least 5 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline. Preferably, the particles comprise at least 10 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

Typically, the condensation aerosol has a mass of at least 10 μg. Preferably, the aerosol has a mass of at least 100 μg. More preferably, the aerosol has a mass of at least 200 μg.

Typically, the particles comprise less than 10 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products. Preferably, the particles comprise less than 5 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products. More preferably, the particles comprise 2.5, 1, 0.5, 0.1 or 0.03 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, where the aerosol comprises bupropion, the delivered aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 20 mg/L and 150 mg/L.

Typically, where the aerosol comprises nefazodone, the delivered aerosol has an inhalable aerosol drug mass density of between 5 mg/L and 250 mg/L. Preferably, the aerosol has an inhalable aerosol drug mass density of between 10 mg/L and 225 mg/L. More preferably, the aerosol has an inhalable aerosol drug mass density of between 20 mg/L and 200 mg/L.

Typically, where the aerosol comprises perphenazine, the delivered aerosol has an inhalable aerosol drug mass density of between 0.2 mg/L and 5 mg/L. Preferably, the aerosol has an inhalable aerosol drug mass density of between 0.5 mg/L and 4 mg/L. More preferably, the aerosol has an inhalable aerosol drug mass density of between 0.5 mg/L and 3 mg/L.

Typically, where the aerosol comprises trazodone, the delivered aerosol has an inhalable aerosol drug mass density of between 5 mg/L and 200 mg/L. Preferably, the aerosol has an inhalable aerosol drug mass density of between 10 mg/L and 150 mg/L. More preferably, the aerosol has an inhalable aerosol drug mass density of between 20 mg/L and 100 mg/L.

Typically, where the aerosol comprises trimipramine, the delivered aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 15 mg/L and 150 mg/L.

Typically, where the aerosol comprises venlafaxine, the delivered aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 15 mg/L and 100 mg/L.

Typically, where the aerosol comprises tranylcypromine, the delivered aerosol has an inhalable aerosol drug mass density of between 3 mg/L and 30 mg/L. Preferably, the aerosol has an inhalable aerosol drug mass density of between 7.5 mg/L and 25 mg/L. More preferably, the aerosol has an inhalable aerosol drug mass density of between 7.5 mg/L and 20 mg/L.

Typically, where the aerosol comprises citalopram, the delivered aerosol has an inhalable aerosol drug mass density of between 4 mg/L and 40 mg/L. Preferably, the aerosol has an inhalable aerosol drug mass density of between 10 mg/L and 35 mg/L. More preferably, the aerosol has an inhalable aerosol drug mass density of between 10 mg/L and 30 mg/L.

Typically, where the aerosol comprises fluoxetine, the delivered aerosol has an inhalable aerosol drug mass density of between 4 mg/L and 40 mg/L. Preferably, the aerosol has an inhalable aerosol drug mass density of between 10 mg/L and 35 mg/L. More preferably, the aerosol has an inhalable aerosol drug mass density of between 10 mg/L and 30 mg/L.

Typically, where the aerosol comprises fluvoxamine, the delivered aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises mirtazepine, the delivered aerosol has an inhalable aerosol drug mass density of between 3 mg/L and 30 mg/L. Preferably, the aerosol has an inhalable aerosol drug mass density of between 7.5 mg/L and 25 mg/L. More preferably, the aerosol has an inhalable aerosol drug mass density of between 7.5 mg/L and 20 mg/L.

Typically, where the aerosol comprises paroxetine, the delivered aerosol has an inhalable aerosol drug mass density of between 2 mg/L and 50 mg/L. Preferably, the aerosol has an inhalable aerosol drug mass density of between 5 mg/L and 40 mg/L. More preferably, the aerosol has an inhalable aerosol drug mass density of between 5 mg/L and 30 mg/L.

Typically, where the aerosol comprises sertraline, the delivered aerosol has an inhalable aerosol drug mass density of between 5 mg/L and 100 mg/L. Preferably, the aerosol has an inhalable aerosol drug mass density of between 10 mg/L and 80 mg/L. More preferably, the aerosol has an inhalable aerosol drug mass density of between 15 mg/L and 50 mg/L.

Typically, where the aerosol comprises amoxapine, the delivered aerosol has an inhalable aerosol drug mass density of between 5 mg/L and 200 mg/L. Preferably, the aerosol has an inhalable aerosol drug mass density of between 10 mg/L and 175 mg/L. More preferably, the aerosol has an inhalable aerosol drug mass density of between 20 mg/L and 150 mg/L.

Typically, where the aerosol comprises clomipramine, the delivered aerosol has an inhalable aerosol drug mass density of between 5 mg/L and 200 mg/L. Preferably, the aerosol has an inhalable aerosol drug mass density of between 10 mg/L and 150 mg/L. More preferably, the aerosol has an inhalable aerosol drug mass density of between 20 mg/L and 100 mg/L.

Typically, where the aerosol comprises doxepin, the delivered aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 20 mg/L and 100 mg/L.

Typically, where the aerosol comprises imipramine, the delivered aerosol has an inhalable aerosol drug mass density of between 5 mg/L and 150 mg/L. Preferably, the aerosol has an inhalable aerosol drug mass density of between 10 mg/L and 125 mg/L. More preferably, the aerosol has an inhalable aerosol drug mass density of between 20 mg/L and 100 mg/L.

Typically, where the aerosol comprises maprotiline, the delivered aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises nortriptyline, the delivered aerosol has an inhalable aerosol drug mass density of between 5 mg/L and 100 mg/L. Preferably, the aerosol has an inhalable aerosol drug mass density of between 10 mg/L and 75 mg/L. More preferably, the aerosol has an inhalable aerosol drug mass density of between 20 mg/L and 50 mg/L.

Typically, where the aerosol comprises valproic acid, the delivered aerosol has an inhalable aerosol drug mass density of between 20 mg/L and 1000 mg/L. Preferably, the aerosol has an inhalable aerosol drug mass density of between 50 mg/L and 500 mg/L. More preferably, the aerosol has an inhalable aerosol drug mass density of between 100 mg/L and 400 mg/L.

Typically, where the aerosol comprises protriptyline, the delivered aerosol has an inhalable aerosol drug mass density of between 3 mg/L and 30 mg/L. Preferably, the aerosol has an inhalable aerosol drug mass density of between 5 mg/L and 25 mg/L. More preferably, the aerosol has an inhalable aerosol drug mass density of between 7.5 mg/L and 20 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, where the aerosol comprises bupropion, between 5 mg and 200 mg of bupropion are delivered to the mammal in a single inspiration. Preferably, between 10 mg and 175 mg of bupropion are delivered to the mammal in a single inspiration. More preferably, between 20 mg and 150 mg of bupropion are delivered to the mammal in a single inspiration.

Typically, where the aerosol comprises nefazodone, between 5 mg and 250 mg of nefazodone are delivered to the mammal in a single inspiration. Preferably, between 10 mg and 225 mg are delivered to the mammal in a single inspiration. More preferably, between 20 mg and 200 mg of nefazodone are delivered to the mammal in a single inspiration.

Typically, where the aerosol comprises perphenazine, between 0.2 mg and 5 mg of perphenazine are delivered to the mammal in a single inspiration. Preferably, between 0.5 mg and 4 mg of perphenazeine are delivered to the mammal in a single inspiration. More preferably, between 0.5 mg and 3 mg of perphenazine are delivered to the mammal in a single inspiration.

Typically, where the aerosol comprises trazodone, between 5 mg and 200 mg of trazodone are delivered to the mammal in a single inspiration. Preferably, between 10 mg and 150 mg of trazodone are delivered to the mammal in a single inspiration. More preferably, between 20 mg and 100 mg of trazodone are delivered to the mammal in a single inspiration.

Typically, where the aerosol comprises trimipramine, between 5 mg 200 mg of trimipramine are delivered to the mammal in a single inspiration. Preferably, between 10 mg and 175 mg of trimipramine are delivered to the mammal in a single inspiration. More preferably, between 20 mg and 150 mg of trimipramine are delivered to the mammal in a single inspiration.

Typically, where the aerosol comprises venlafaxine, between 5 mg and 150 mg of venlafaxine are delivered to the mammal in a single inspiration. Preferably, between 10 mg and 125 mg of venlafaxine are delivered to the mammal in a single inspiration. More preferably, between 20 mg and 100 mg of venlafaxine are delivered to the mammal in a single inspiration.

Typically, where the aerosol comprises tranylcypromine, between 3 mg and 30 mg of tranylcypromine are delivered to the mammal in a single inspiration. Preferably, between 7.5 mg and 25 mg of tranylcypromine are delivered to the mammal in a single inspiration. More preferably, between 7.5 mg and 20 mg of tranylcypromine are delivered to the mammal.

Typically, where the aerosol comprises citalopram, between 4 mg and 40 mg of citalopram are delivered to the mammal in a single inspiration. Preferably, between 10 mg and 35 mg of citalopram are delivered to the mammal in a single inspiration. More preferably, between 10 mg and 30 mg of citalopram are delivered to the mammal in a single inspiration.

Typically, where the aerosol comprises fluoxetine, between 4 mg and 40 mg of fluoxetine are delivered to the mammal in a single inspiration. Preferably, between 10 mg and 35 mg of fluoxetine are delivered to the mammal in a single inspiration. More preferably, between 10 mg and 30 mg of fluoxetine are delivered to the mammal in a single inspiration.

Typically, where the aerosol comprises fluvoxamine, between 5 mg and 100 mg of fluvoxamine are delivered to the mammal in a single inspiration. Preferably, between 10 mg and 75 mg of fluvoxamine are delivered to the mammal in a single inspiration. More preferably, between 20 mg and 50 mg of fluvoxamine are delivered to the mammal in a single inspiration.

Typically, where the aerosol comprises mirtazepine, between 3 mg and 30 mg of mirtazepine are delivered to the mammal in a single inspiration. Preferably, between 7.5 mg and 25 mg of mirtazepine are delivered to the mammal in a single inspiration. More preferably, between 7.5 mg and 20 mg of mirtazepine are delivered to the mammal in a single inspiration.

Typically, where the aerosol comprises paroxetine, between 2 mg and 50 mg of paroxetine are delivered to the mammal in a single inspiration. Preferably, between 5 mg and 40 mg of paroxetine are delivered to the mammal in a single inspiration. More preferably, between 5 mg and 30 mg of paroxetine are delivered to the mammal in a single inspiration.

Typically, where the aerosol comprises sertraline, between 5 mg and 100 mg of sertraline are delivered to the mammal in a single inspiration. Preferably, between 10 mg and 80 mg of sertraline are delivered to the mammal in a single inspiration. More preferably, between 15 mg and 50 mg of sertraline are delivered to the mammal in a single inspiration.

Typically, where the aerosol comprises amoxapine, between 5 mg and 200 mg of amoxapine are delivered to the mammal in a single inspiration. Preferably, between 10 mg and 175 mg of sertraline are delivered to the mammal in a single inspiration. More preferably, between 20 mg and 150 mg of amoxapine are delivered to the mammal in a single inspiration.

Typically, where the aerosol comprises clomipramine, between 5 mg and 200 mg of clomipramine are delivered to the mammal in a single inspiration. Preferably, between 10 mg and 150 mg of clomipramine are delivered to the mammal in a single inspiration. More preferably, between 20 mg and 100 mg of clomipramine are delivered to the mammal in a single inspiration.

Typically, where the aerosol comprises doxepin, between 5 mg and 150 mg of doxepin are delivered to the mammal in a single inspiration. Preferably, between 10 mg and 125 mg of doxepin are delivered to the mammal in a single inspiration. More preferably, between 20 mg and 100 mg of doxepin are delivered to the mammal in a single inspiration.

Typically, where the aerosol comprises imipramine, between 5 mg and 150 mg of imipramine are delivered to the mammal in a single inspiration. Preferably, between 10 mg and 125 mg of imipramine are delivered to the mammal in a single inspiration. More preferably, between 20 mg and 100 mg of imipramine are delivered to the mammal in a single inspiration.

Typically, where the aerosol comprises maprotiline, between 5 mg and 100 mg of maprotiline are delivered to the mammal in a single inspiration. Preferably, between 10 mg and 75 mg of maprotiline are delivered to the mammal in a single inspiration. More preferably, between 20 mg and 50 mg of maprotiline are delivered to the mammal in a single inspiration.

Typically, where the aerosol comprises nortriptyline, between 5 mg and 100 mg of nortriptyline are delivered to the mammal in a single inspiration. Preferably, between 10 mg and 75 mg of nortriptyline are delivered to the mammal in a single inspiration. More preferably, between 20 mg and 50 mg of nortriptyline are delivered to the mammal in a single inspiration.

Typically, where the aerosol comprises valproic acid, between 20 mg and 1000 mg of valproic acid are delivered to the mammal in a single inspiration. Preferably, between 50 mg and 500 mg of valproic acid are delivered to the mammal in a single inspiration. More preferably, between 100 mg and 400 mg of valproic acid are delivered to the mammal in a single inspiration Typically, where the aerosol comprises protriptyline, between 3 mg and 30 mg of protriptyline are delivered to the mammal in a single inspiration. Preferably, between 5 mg and 25 mg of protriptyline are delivered to the mammal in a single inspiration. More preferably, between 7.5 mg and 20 mg of protriptyline are delivered to the mammal in a single inspiration.

Typically, the delivered condensation aerosol results in a peak plasma concentration of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline in the mammal in less than 1 h. Preferably, the peak plasma concentration is reached in less than 0.5 h. More preferably, the peak plasma concentration is reached in less than 0.2, 0.1, 0.05, 0.02, 0.01 h, or 0.005 h (arterial measurement).

Typically, the delivered condensation aerosol is used to treat depression.

In a kit aspect of the present invention, a kit for delivering an antidepressant through an inhalation route to a mammal is provided which comprises: a) a composition comprising at least 5 percent by weight of an antidepressant; and, b) a device that forms an antidepressant aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antidepressant.

Typically, the device contained in the kit comprises: a) an element for heating the antidepressant composition to form a vapor; b) an element allowing the vapor to cool to form an aerosol; and, c) an element permitting the mammal to inhale the aerosol.

Typically, the antidepressant is selected from one of the following five classes of antidepressants: tricyclic antidepressants; tetracyclic antidepressants; selective serotonin reuptake inhibitors; monoamine oxidase inhibitors; and, atypical antidepressants.

In another kit aspect of the present invention, a kit for delivering bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline through an inhalation route to a mammal is provided which comprises: a) a composition comprising at least 5 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline; and, b) a device that forms an bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

Typically, the device contained in the kit comprises: a) an element for heating the bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
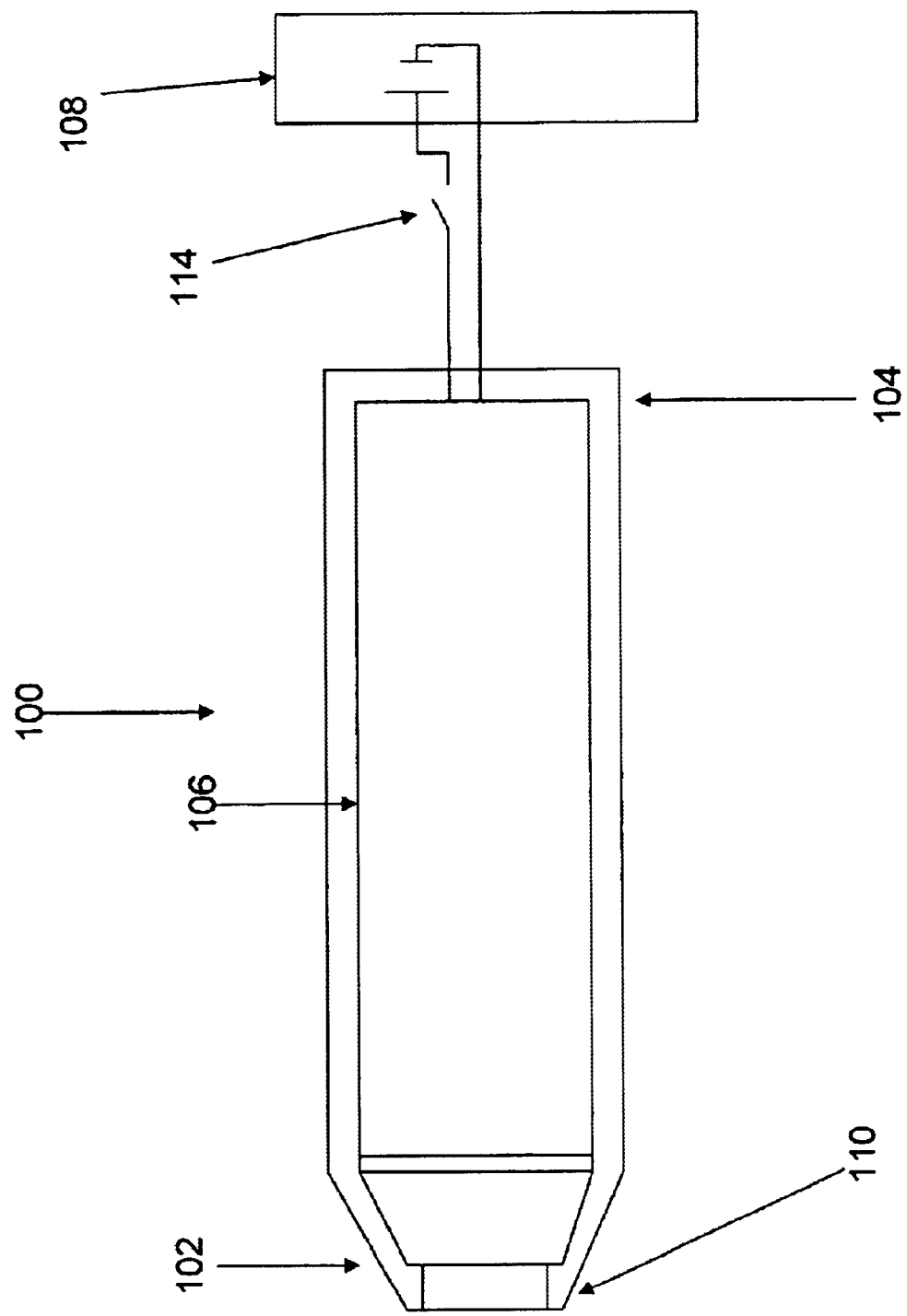
FIG. 1 shows a cross-sectional view of a device used to deliver antidepressant aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of antidepressant per unit volume of aerosol.

"Aerosol mass density" refers to the mass of particulate matter per unit volume of aerosol.

"Aerosol particle density" refers to the number of particles per unit volume of aerosol.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Amoxapine" refers to 2-chloro-11-(1-piperazinyl) dibenz-[b,f] [1,4]oxapine.

"Amoxapine degradation product" refers to a compound resulting from a chemical modification of amoxapine. The modification, for example, can be the result of a thermally or photochemically induced reaction. Such reactions include, without limitation, oxidation and hydrolysis.

"Antidepressant degradation product" refers to a compound resulting from a chemical modification of an antidepressant. The modification, for example, can be the result of a thermally or photochemically induced reaction. Such reactions include, without limitation, oxidation and hydrolysis.

"Bupropion" refers to (±)-1-(3-chlorophenyl)-2-[(1,1-dimethylethyl)aminol-1-propanone.

"Bupropion degradation product" refers to a compound resulting from a chemical modification of bupropion. The modification, for example, can be the result of a thermally or photochemically induced reaction. Such reactions include, without limitation, oxidation and hydrolysis.

"Citalopram" refers to (±)-1-(3-dimethyl-aminopropyl)-1-(4-fluorophenyl-1,3-dihydroisobenzofuran-5-carbonitrile.

"Citalopram degradation product" refers to a compound resulting from a chemical modification of citalopram. The modification, for example, can be the result of a thermally or photochemically induced reaction. Such reactions include, without limitation, oxidation and hydrolysis.

"Clomipramine" refers to 3-chloro-10,11-dihydro-N,N-dimethyl-5H-dibenz[b,f]azepine-5-propanamine.

"Clomipramine degradation product" refers to a compound resulting from a chemical modification of clomipramine. The modification, for example, can be the result of a thermally or photochemically induced reaction. Such reactions include, without limitation, oxidation and hydrolysis.

"Condensation aerosol" refers to an aerosol formed by vaporization of a substance followed by condensation of the substance into an aerosol.

"Doxepin" refers to 3-dibenz[b,e]oxepin-11(6H)-ylidene-N,N-dimethyl-1-propanamine.

"Doxepin degradation product" refers to a compound resulting from a chemical modification of doxepin. The modification, for example, can be the result of a thermally or photochemically induced reaction. Such reactions include, without limitation, oxidation and hydrolysis.

"Fluoxetine" refers to (±)-N-methyl-3-phenyl-3-[(α,α,α-trifluoro-p-tolyl)oxy]propylamine.

"Fluoxetine degradation product" refers to a compound resulting from a chemical modification of fluoxetine. The modification, for example, can be the result of a thermally or photochemically induced reaction. Such reactions include, without limitation, oxidation and hydrolysis. Examples of fluoxetine degradation products include 4-(trifluoromethyl)-phenol and 3-phenyl-2-propenal.

"Fluvoxamine" refers to 5-methoxy-4'-(trifluoromethyl) valero-phenone-(E)-O-(2-aminoethyl)oxime.

"Fluvoxamine degradation product" refers to a compound resulting from a chemical modification of fluvoxamine. The modification, for example, can be the result of a thermally or photochemically induced reaction. Such reactions include, without limitation, oxidation and hydrolysis.

"Imipramine" refers to 10,11-dihydro-N,N-dimethyl-5H-dibenz [b,f]azepine-5-propanamine.

"Imipramine degradation product" refers to a compound resulting from a chemical modification of imipramine. The modification, for example, can be the result of a thermally or photochemically induced reaction. Such reactions include, without limitation, oxidation and hydrolysis.

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Maprotiline" refers to N-methyl-9,10-ethano-anthracene-9(10H)-propanamine.

"Maprotiline degradation product" refers to a compound resulting from a chemical modification of maprotiline. The modification, for example, can be the result of a thermally or photochemically induced reaction. Such reactions include, without limitation, oxidation and hydrolysis.

"Mirtazepine" refers to 1,2,3,4,10,14b-hexahydro-2-methyl-pyrazino [2,1-a] pyrido [2,3-c] benzazepine.

"Mirtazepine degradation product" refers to a compound resulting from a chemical modification of mirtazepine. The modification, for example, can be the result of a thermally or photochemically induced reaction. Such reactions include, without limitation, oxidation and hydrolysis.

"Nefazodone" refers to 2-[3-[4-(3-chlorophenyl)-1-piperazinyl]propyl]-5-ethyl-2,4-dihydro-4-(2-phenoxyethyl)-3H-1,2,4-triazol-3-one "Nefazodone degradation product" refers to a compound resulting from a chemical modification of nefazodone. The modification, for example, can be the result of a thermally or photochemically induced reaction. Such reactions include, without limitation, oxidation and hydrolysis.

"Nortriptylene" refers to 3-(10,11-dihydro-5H-dibenzo[a,d]-cyclo-hepten-5-ylidene)-N-methyl-1-propanamine.

"Nortriptylene degradation product" refers to a compound resulting from a chemical modification of nortriptylene. The modification, for example, can be the result of a thermally or photochemically induced reaction. Such reactions include, without limitation, oxidation and hydrolysis.

"Paroxetine" refers to (−)-trans-4R-(4'-fluorophenyl)-3S-[(3',4'-methylene-dioxyphenoxy)methyl] piperidine.

"Paroxetine degradation product" refers to a compound resulting from a chemical modification of paroxetine. The modification, for example, can be the result of a thermally or photochemically induced reaction. Such reactions include, without limitation, oxidation and hydrolysis.

"Perphenazine" refers to 4-[3-(2-chlorophenothiazin-10-yl)propyl]-1-piperazineethanol.

"Perphenazine degradation product" refers to a compound resulting from a chemical modification of perphenazine. The modification, for example, can be the result of a thermally or photochemically induced reaction. Such reactions include, without limitation, oxidation and hydrolysis.

"Protriptylene" refers to N-methyl-5H-dibenzo [a,d] cycloheptene-5-propylamine

"Protriptylene degradation product" refers to a compound resulting from a chemical modification of protriptylene. The modification, for example, can be the result of a thermally or photochemically induced reaction. Such reactions include, without limitation, oxidation and hydrolysis.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of antidepressant produced by an inhalation device per unit time.

"Sertraline" refers to (1S-cis)-4-(3,4-dichlorophenyl)-1,2,3,4-tetrahydro-N-methyl-1-naphthalen-amine.

"Sertraline degradation product" refers to a compound resulting from a chemical modification of sertraline. The modification, for example, can be the result of a thermally or photochemically induced reaction. Such reactions include, without limitation, oxidation and hydrolysis.

"Settling velocity" refers to the terminal velocity of an aerosol particle undergoing gravitational settling in air.

"Trazodone" refers to 2-[3-[4 -(3-chlorophenyl)-1-piperazinyl]propyl]-1,2,4-triazolo[4,3-a]pyridine-3(2H)-one.

"Trazodone degradation product" refers to a compound resulting from a chemical modification of trazodone. The modification, for example, can be the result of a thermally or photochemically induced reaction. Such reactions include, without limitation, oxidation and hydrolysis.

"Tranylcypromine" refers to (±)-trans-2-phenyl-cyclopropylamine.

"Tranylcypromine degradation product" refers to a compound resulting from a chemical modification of tranylcypromine. The modification, for example, can be the result of a thermally or photochemically induced reaction. Such reactions include, without limitation, oxidation and hydrolysis.

"Trimipramine" refers to 10,11-dihydro-N,N,β-trimethyl-5H-dibenz [b,f]azepine-5-propanamine.

"Trimipramine degradation product" refers to a compound resulting from a chemical modification of trimipramine. The modification, for example, can be the result of a thermally or photochemically induced reaction. Such reactions include, without limitation, oxidation and hydrolysis.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

"Valproic acid" refers to 2-propylpentanoic acid.

"Valproic acid degradation product" refers to a compound resulting from a chemical modification of valproic acid. The modification, for example, can be the result of a thermally or photochemically induced reaction. Such reactions include, without limitation, oxidation and hydrolysis.

"Venlafaxine" refers to (R/S)-1-[2-(dimethyl-amino)-1-(4-methoxy-phenyl)ethyl] cyclohexanol.

"Venlafaxine degradation product" refers to a compound resulting from a chemical modification of venlafaxine. The modification, for example, can be the result of a thermally or photochemically induced reaction. Such reactions include, without limitation, oxidation and hydrolysis.

Formation of Antidepressant Containing Aerosols

Any suitable method is used to form the aerosols of the present invention. A preferred method, however, involves heating a composition comprising an antidepressant to form a vapor, followed by cooling of the vapor such that it condenses to provide an antidepressant comprising aerosol (condensation aerosol). The composition is heated in one of four forms: as pure active compound (e.g., pure bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline); as a mixture of active compound and a pharmaceutically acceptable excipient; as a salt form of the pure active compound; and, as a mixture of active compound salt form and a pharmaceutically acceptable excipient.

Salt forms of antidepressants (e.g., bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline) are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with the antidepressants. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the antidepressant compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Antidepressant Containing Aerosols

Antidepressant containing aerosols of the present invention are delivered to a mammal using an inhalation device. Where the aerosol is a condensation aerosol, the device has at least three elements: an element for heating an antidepressant containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the antidepressant containing aerosol is described in reference to FIG. 1. Delivery device 100 has a proximal end 102 and a distal end 104, a heating module 106, a power source 108, and a mouthpiece 110. An antidepressant composition is deposited on a surface 112 of heating module 106. Upon activation of a user activated switch 114, power source 108 initiates heating of heating module 106 (e.g, through ignition of combustible fuel or passage of current through a resistive heating element). The antidepressant composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of antidepressant containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Antidepressant Containing Aerosols

The dosage amount of an antidepressant in aerosol form is generally no greater than twice the standard dose of the drug given orally. The following are typical dosages of exemplary compounds for the treatment of depression: bupropion (100 mg), nefazodone (150 mg), perphenazine (2 mg), trazodone (50–100 mg), trimipramine (50–100 mg), venlafaxine (75 mg), tranylcypromine (15 mg), citalopram (20 mg), fluoxetine (20 mg), fluvoxamine (50 mg), mirtazepine (15 mg), paroxetine (10–25 mg), sertraline (25–50 mg), amoxapine (25–250 mg), clomipramine (100 mg), doxepin (75 mg), imipramine (75 mg), maprotiline (50 mg), nortriptyline (50 mg), valproic acid (250 mg) and protryptyline (15 mg). As aerosols, the compounds are generally provided in the following amounts per inspiration for the same indication: bupropion (5–200 mg), nefazodone (5–250 mg), perphenazine (0.2–5 mg), trazodone (5–200 mg), trimipramine (5–200 mg), venlafaxine (5–150 mg), tranylcypromine (3–30 mg), citalopram (4–40 mg), fluoxetine (4–40 mg), fluvoxamine (5–100 mg), mirtazepine (3–30 mg), paroxetine (2–50 mg), sertraline (5–100 mg), amoxapine (5–200 mg), clomipramine (5–200 mg), doxepin (5–150 mg), imipramine (5–150 mg), maprotiline (5–100 mg), nortriptylene (5–100 mg), valproic acid (20–1000 mg) and protriptyline (3–30 mg). A typical dosage of an antidepressant aerosol is either administered as a single inhalation or as a series of inhalations taken within an hour or less (dosage equals sum of inhaled amounts). Where the drug is administered as a series of inhalations, a different amount may be delivered in each inhalation.

One can determine the appropriate dose of an antidepressant containing aerosol to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Antidepressant Containing Aerosols

Purity of an antidepressant containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of antidepressant degradation products.

Particle size distribution of an antidepressant containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles= Sum (from size range 1 to size range N) of number of particles in each size range. Number of particles in a given size range=Mass in the size range/Mass of a typical particle in the size range. Mass of a typical particle in a given size range=$\pi * D^3 * \phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering an antidepressant containing aerosol into a confined chamber via an inhalation device over a set period of time (e.g., 3 s). Where the aerosol is pure antidepressant, the amount of drug collected in the chamber is measured as described above. The rate of drug aerosol formation is equal to the amount of antidepressant collected in the chamber divided by the duration of the collection time. Where the antidepressant containing aerosol comprises a pharmaceutically acceptable excipient, multiplying the rate of aerosol formation by the percentage of antidepressant in the aerosol provides the rate of drug aerosol formation.

Utility of Antidepressant Containing Aerosols

The antidepressant containing aerosols of the present invention are typically used for the treatment of depression. Valproic acid is also typically used for the treatment of mania.

The following examples are meant to illustrate, rather than limit, the present invention.

Bupropion hydrochloride, perphenazine, trazodone hydrochloride, trimipramine maleate, tranylcypromine hydrochloride, citalopram hydrobromide, fluoxetine hydrochloride, fluvoxamine maleate, amoxapine, clomipramine hydrochloride, doxepin hydrochloride, imipramine hydrochloride, valproic acid, and maprotiline hydrochloride are commercially available from Sigma (www.sigma-aldrich.com). Nefazodone hydrochloride (SERZONE®), venlafaxine hydrochloride (EFFEXOR®), mirtazepine (REMERON®), paroxetine hydrochloride (PAXIL®), sertraline hydrochloride (ZOLOFT®), nortriptyline hydrochloride (Mylan), and protriptylene hydrochloride (VIVACTIL®) are commercially available, and the active ingredient can be isolated using standard methods in the art.

EXAMPLE 1

General Procedure for Obtaining Free Base of a Compound Salt

Approximately 1 g of salt (e.g., mono hydrochloride) is dissolved in deionized water (~30 mL). Three equivalents of sodium hydroxide (1 N $NaOH_{aq}$) is added dropwise to the solution, and the pH is checked to ensure it is basic. The aqueous solution is extracted four times with dichloromethane (~50 mL), and the extracts are combined, dried ($Na_2SO_4$) and filtered. The filtered organic solution is concentrated using a rotary evaporator to provide the desired free base. If necessary, purification of the free base is performed using standard methods such as chromatography or recrystallization.

EXAMPLE 2

General Procedure for Volatilizing Compounds from Halogen Bulb

A solution of drug in approximately 120 µL dichloromethane is coated on a 3.5 cm×7.5 cm piece of aluminum foil (precleaned with acetone). The dichloromethane is allowed to evaporate. The coated foil is wrapped around a 300 watt halogen tube (Feit Electric Company, Pico Rivera, Calif.), which is inserted into a glass tube sealed at one end with a rubber stopper. Running 90 V of alternating current (driven by line power controlled by a variac) through the bulb for 3.5 s (2 mg coating) or 5 s (10 mg coating) affords thermal vapor (including aerosol), which is collected on the glass tube walls. (When desired, the system is flushed through with argon prior to volatilization.) Reverse-phase HPLC analysis with detection by absorption of 225 nm light is used to determine the purity of the aerosol.

Table 1, which follows, provides data from drugs volatilized using the above-recited general procedure. To obtain higher purity aerosols, one can coat a lesser amount of drug, yielding a thinner film to heat. A linear decrease in film thickness is associated with a linear decrease in impurities.

TABLE 1

| COMPOUND | PURITY | AEROSOL MASS | ARGON |
| --- | --- | --- | --- |
| Bupropion Hydrochloride | 98.5% | 2.1 mg | No |
|  | 99.1% | 1.8 mg | Yes |
| Nefazodone | 96.5% | 0.23 mg | No |
|  | 98.5% | 0.66 mg | Yes |
| Perphenazine | 99.1% | 0.37 mg | No |
|  | 98.6% | 0.44 mg | Yes |
| Trazodone | 97.9% | 0.64 mg | No |
|  | 98.5% | 0.56 mg | Yes |
| Trimipramine Maleate | 95.9% | 1.6 mg | No |
|  | 97.4% | 2.1 mg | Yes |
| Venlafaxine | 99.4% | 1.65 mg | No |
|  | 99.9% | 1.80 mg | Yes |
| Tranylcypromine Hydrochloride | 97.5% | 1.3 mg | No |
|  | 97.2% | 1.2 mg | Yes |
| Citalopram | 94.7% | 3.4 mg | No |
|  | 95.6% | 3.0 mg | Yes |
| Fluoxetine | 97.4% | 1.4 mg | No |
|  | 96.8% | 1.7 mg | Yes |
| Mirtazepine | 99.6% | 1.8 mg | No |
|  | 99.5% | 2.3 mg | Yes |
| Paroxetine | 96.0% | 1.7 mg | No |
|  | 96.3% | 1.8 mg | Yes |
| Sertraline | 98.6% | 1.30 mg | No |
|  | 98.7% | 1.29 mg | Yes |
| Amoxapine | 98.5% | 1.6 mg | No |
|  | 99.2% | 1.6 mg | Yes |
| Clomipramine | 96.0% | 1.6 mg | No |
|  | 97.7% | 1.5 mg | Yes |
| Doxepin | 99.0% | 2.2 mg | No |
|  | 99.1% | 2.1 mg | Yes |
| Imipramine | 98.3% | 1.9 mg | No |
|  | 99.1% | 1.5 mg | Yes |
| Maprotiline | 99.7% | 1.3 mg | No |
|  | 99.6% | 1.5 mg | Yes |
| Nortriptyline | 99.1% | 1.4 mg | No |
|  | 97.8% | 1.6 mg | Yes |
| Protriptylene Hydrochloride | 99.7% | 0.99 mg | No |
|  | 99.8% | 1.1 mg | Yes |

EXAMPLE 3

Particle Size, Particle Density, and Rate of InhalableParticle Formation of Paroxetine Aerosol A solution of 22.0 mg paroxetine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with ten needles for flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 2.0 microns with a geometric standard deviation of 1.9. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm$^3$). The inhalable aerosol particle density is the sum of the numbers of particles collected on impactor stages 3 to 8 divided by the collection volume of 1 L, giving an inhalable aerosol particle density of $9.0 \times 10^6$ particles/mL. The rate of inhalable aerosol particle formation is the sum of the numbers of particles collected on impactor stages 3 through 8 divided by the formation time of 6 s, giving a rate of inhalable aerosol particle formation of $1.5 \times 10^9$ particles/second.

TABLE 1

Determination of the characteristics of a paroxetine condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.1 | $2.2 \times 10^5$ |
| 1 | 5.8–9.0 | 7.4 | 0.4 | $1.9 \times 10^6$ |
| 2 | 4.7–5.8 | 5.25 | 0.3 | $4.0 \times 10^6$ |
| 3 | 3.3–4.7 | 4.0 | 1.4 | $4.2 \times 10^7$ |
| 4 | 2.1–3.3 | 2.7 | 2.6 | $2.5 \times 10^8$ |
| 5 | 1.1–2.1 | 1.6 | 3.9 | $1.8 \times 10^9$ |
| 6 | 0.7–1.1 | 0.9 | 1.3 | $3.4 \times 10^9$ |
| 7 | 0.4–0.7 | 0.55 | 0.3 | $3.4 \times 10^9$ |
| 8 | 0–0.4 | 0.2 | 0.0 | 0 |

EXAMPLE 4

Drug Mass Density and Rate of Drug Aerosol Formation of Paroxetine Aerosol

A solution of 19.6 mg paroxetine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with ten needles for flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of paroxetine revealed that 3.4 mg of >88% pure paroxetine had been collected in the flask, resulting in an aerosol drug mass density of 3.4 mg/L. The aluminum foil upon which the paroxetine had previously been coated was weighed following the experiment. Of the 19.6 mg originally coated on the aluminum, 7.4 mg of the material was found to have aerosolized in the 6 s time period, implying a rate of drug aerosol formation of 1.2 mg/s.

EXAMPLE 5

Particle Size, Particle Density, and Rate of InhalableParticle Formation of Mirtazepine Aerosol A solution of 18.7 mg mirtazepine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with ten needles for air flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 1.2 microns with a geometric standard deviation of 2.2. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm$^3$). The inhalable aerosol particle density is the sum of the numbers of particles collected on impactor stages 3 to 8 divided by the collection volume of 1 L, giving an inhalable aerosol particle density of $5.6 \times 10^7$ particles/mL. The rate of inhalable aerosol particle formation is the sum of the numbers of particles collected on impactor stages 3 through 8 divided by the formation time of 6 s, given a rate of inhalable aerosol partical formation of $9.3 \times 10^6$ particals/second.

TABLE 1

Determination of the characteristics of a mirtazepine condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.0 | 0 |
| 1 | 5.8–9.0 | 7.4 | 0.1 | $4.7 \times 10^5$ |
| 2 | 4.7–5.8 | 5.25 | 0.0 | 0 |
| 3 | 3.3–4.7 | 4.0 | 0.2 | $6.0 \times 10^6$ |

TABLE 1-continued

Determination of the characteristics of a mirtazepine condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 4 | 2.1–3.3 | 2.7 | 0.4 | $3.9 \times 10^7$ |
| 5 | 1.1–2.1 | 1.6 | 0.9 | $4.2 \times 10^8$ |
| 6 | 0.7–1.1 | 0.9 | 0.8 | $2.1 \times 10^9$ |
| 7 | 0.4–0.7 | 0.55 | 0.5 | $5.7 \times 10^9$ |
| 8 | 0–0.4 | 0.2 | 0.2 | $4.8 \times 10^{10}$ |

EXAMPLE 6

Drug Mass Density and Rate of Drug Aerosol Formation of Mirtazepine Aerosol

A solution of 20.7 mg mirtazepine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with ten needles for air flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of mirtazepine revealed that 10.65 mg of >99% pure mirtazepine had been collected in the flask, resulting in an aerosol drug mass density of 10.65 mg/L. The aluminum foil upon which the mirtazepine had previously been coated was weighed following the experiment. Of the 20.7 mg originally coated on the aluminum, 18.7 mg of the material was found to have aerosolized in the 6 s time period, implying a rate of drug aerosol formation of 3.1 mg/s.

EXAMPLE 7

Volatilization of Valproic Acid

Valproic acid (~90 mg) was adsorbed onto a piece of glass wool. The coated glass wool was inserted into a glass tube in a furnace (tube furnace). A glass wool plug was placed in the tube adjacent to the foil sheet, and an air flow of 2 L/min was applied. The furnace was heated to 300° C. for 120 s to volatilize the coated valproic acid and then was allowed to cool. The glass wool was extracted, and HPLC analysis of the collected material showed it to be at least 99.5% pure valproic acid.

We claim:

1. A composition for delivery of an antidepressant drug comprising a condensation aerosol
  a) formed by volatizing an antidepressant drug under conditions effective to produce a heated vapor of the drug and condensing the heated vapor of the drug to form condensation aerosol particles,
  b) wherein said condensation aerosol particles are characterized by less than 5% antidepressant drug degradation products, and
  c) the aerosol has an MMAD less than 3 microns.

2. A composition for delivery of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline comprising a condensation aerosol
  a) formed by volatizing bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline under conditions effective to produce a heated vapor of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protrvotyline and condensing the heated vapor of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline to form condensation aerosol particles,
  b) wherein said condensation aerosol particles are characterized by less than 5% bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline drug degradation products, and
  c) the aerosol has an MMAD less than 3 microns.

3. The composition according to claim 2, wherein the condensation aerosol particles comprise at least 90 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

4. The composition according to claim 3, wherein the geometric standard deviation around the mass median aerodynamic diameter of the aerosol is less than 2.5.

5. The composition according to claim 3, wherein the condensation aerosol particles comprise at least 95 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, noriryptiline, valproic acid, or protryptyline.

6. A method of producing an antidepressant drug in an aerosol form comprising:
  a) volatilizing an antidepressant drug under conditions effective to produce a heated vapor of the drug, and
  b) during said volatilizing, passing air through the heated vapor to produce aerosol particles of the drug comprising less than 5% antidepressant drug degradation products and an aerosol having an MMAD less than 3 µm.

7. A method of producing bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, vaiproic acid, or protryptyline in an aerosol form comprising:

a) volatilizing bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptyline, valproic acid, or protryptyline under conditions effective to produce a heated vapor of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryotyline, and b) during said volatilizing, passing air through the heated vapor to produce aerosol particles of the bupropion, nefazodone, perphenazine, trazodone, trimipramine, venlafaxine, tranylcypromine, citalopram, fluoxetine, fluroxamine, mirtazepine, paroxetine, sertraline, amoxapine, clomipramine, doxepin, imipramine, maprotiline, nortryptiline, valproic acid, or protryptyline comprising less than 5% bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline degradation products and an aerosol having an MMAD less than 3 μm.

8. The method according to claim 6, wherein the aerosol particles are formed at a rate of greater than 0.5 mg/sec.

9. The method according to claim 6, wherein said volatilizing includes heating a film, which includes the antidepressant drug and is on a solid support having the surface texture of a metal foil, to a temperature sufficient to volatilize the drug from the film.

10. The method according to claim 7, wherein the aerosol particles comprise at least 90 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, vaiproic acid, or protryptyline.

11. The method according to claim 10, wherein the geometric standard deviation around the mass median aerodynamic diameter of the aerosol is less than 2.5.

12. The method according to claim 11, wherein the aerosol particles comprise at least 95 percent by weight of bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline.

13. The method according to claim 7, wherein said volatilizing includes heating a film, which includes bupropion, nefazodone, perphenazine, trazodone, trimipramine, venlafaxine, tranylcypromine, citalopram, fluoxetine, fluvoxarnine, mirtazepine, paroxetine, sertraline, amoxapane, clomipramine, doxepin, imipramine, maprotiline, nortryptiline, vaiproic acid, or protryptyline and is on solid support having the surface texture of a metal foil, to a temperature sufficient to volatilize the bupropion, nefazodone, perphenazine, trazodone, trimipramine, venlafaxine, tranylcypromine, citalopram, fluoxetine, fluvoxamine, mirtazepine, paroxetine, sertraline, amoxapine, clomipramine, doxepin, imipramine, maprotiline, nortryptiline, valproic acid, or protryptyline from the film.

\* \* \* \* \*